(12) United States Patent
Hatada et al.

(10) Patent No.: US 6,979,731 B1
(45) Date of Patent: Dec. 27, 2005

(54) GENE ENCODING ALKALINE LIQUEFYING α-AMYLASE

(75) Inventors: Yuji Hatada, Tochigi (JP); Katsuya Ozaki, Tochigi (JP); Katsutoshi Ara, Tochigi (JP); Shuji Kawai, Tochigi (JP); Susumu Ito, Tochigi (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 08/952,741

(22) PCT Filed: Jun. 14, 1996

(86) PCT No.: PCT/JP96/01641

§ 371 (c)(1),
(2), (4) Date: Nov. 25, 1997

(87) PCT Pub. No.: WO97/00324

PCT Pub. Date: Jan. 3, 1997

(30) Foreign Application Priority Data

Jun. 14, 1995 (JP) .................................. 7-147257

(51) Int. Cl.$^7$ .......................... C07H 21/04; C12N 9/28; C12N 15/52
(52) U.S. Cl. .................... 536/23.2; 435/202; 435/320.1
(58) Field of Search ............................ 435/202, 282.3, 435/320.1, 832, 209; 536/23.2

(56) References Cited

FOREIGN PATENT DOCUMENTS

| EP | 410498 A3 | 1/1991 |
|---|---|---|
| EP | 670367 A1 | 9/1995 |
| WO | 94 26881 | 11/1994 |
| WO | 95 26397 | 10/1995 |

OTHER PUBLICATIONS

Tsukamoto, et al., "Nucleotide Sequence of the Maltohexaose-Producing Amylase Gene From An Alkalophilic *Bacillus* sp. #707 and Structural Similarity to Liquefying Type α-Amylases," Biochemical and Biophysical Research Communications, vol. 151, No. 1 (Feb. 29, 1988) p.p. 25-31.

Yuuki, et al., "Complete Nucleotide Sequence of a Gene Coding for Heat- and pH-Stable α-Amylase of *Bacillus licheniformis*: Comparison of the Amino Acid Sequences of Three Bacterial Liquefying α-Amylases Deduced from the DNA Sequences," Journal of Biochemistry, vol. 98, No. 5 (1985) p.p. 1147-1156.

Ryoichi Nakajima et al., "Comparison of amino acid sequences of eleven different α-amylases", Applied Microbiology and Biotechnology (1986) 23, pp 335-360.

*Primary Examiner*—Elizabeth Slobodyansky
(74) *Attorney, Agent, or Firm*—Birch, Stewart, Kolasch & Birch, LLP (57) ABSTRACT

The present invention is directed to a liquefying alkaline alpha-amylase, and a DNA encoding for the same and functional fragments thereof.

7 Claims, 4 Drawing Sheets

```
primer 1   5' TAGACGCAGTAAAACACATAAA  3'
              C T C  C G T C
              G   G  G     T
              T   T  T primer 2   3' CGACAATGAAAACAACTATTAGTACT 5'
              G G G G G G G
              C C C   C
              T T T   T primer 3   5' AGCCAATCTCTCGTATAGCTGTA  3' primer 4   5' GTACAAAAACACCCTATACATG  3' primer 5   5' AATGGAACAATGATGCAGTA  3'
                 T T        T primer 6   5' CATTTGGCAAATGCCATTCAAA  3' primer 7   5' AAAATTGATCCACTTCTGCAG  3' primer A   5' CAGCGCGTGATAATATAAATTTGAAT 3' primer B   5' AAGCTTCCAATTTATATTGGGTGTAT 3'
```

FIG. 4

GENE ENCODING ALKALINE LIQUEFYING α-AMYLASE

TECHNICAL FIELD

The present invention relates to the gene encoding alkaline liquefying α-amylase and fragments thereof, and to recombinant DNA and a transformant bearing the gene or fragments of the gene.

BACKGROUND ART

Alpha-amylase has long been used in a variety of fields. For example, it has been used for the saccharification of grains and potatoes in the fermentation industry, as starch paste removers in the textile industry, as digestives in the pharmaceutical industry, and for the manufacture of thick malt syrups in the food industry. Alpha-amylase is an enzyme which acts on a starch-related polysaccharides such as amylose and amylopectin, hydrolyzing solely the α-1,4-glucoside bond of the polysaccharide molecule. Since 1833, when Payen and Persoz first discovered the enzyme, crystalline samples or electrophoretically homogeneous samples of α-amylase have been obtained from a number of different sources including bacteria, fungi, plant seeds, and animal digestive glands.

The present inventors have recently discovered that the efficacy of dish-washing detergents and laundry detergents for clothes can be greatly improved, particularly on starch dirts, when α-amylase and a debranching enzyme are both incorporated into these detergents (Japanese Patent Application Laid-open (kokai) No. 2-132192). However, most of the α-amylases previously found in the natural world exhibit maximal and stable enzymatic activities in the neutral to acidic pH ranges, but scarcely work in an alkaline solution of pH 9–10 There exist only a small number of amylase enzymes that are known to exhibit maximal activities in the alkaline pH range (so-called alkaline α-amylases and alkali-resistant α-amylases). These alkaline α-amylases and alkali-resistant α-amylase include, an enzyme produced by *Bacillus* sp. A-40-2 [Horikoshi, K. et al., *Agric. Biol. Chem.*, 35, 1783 (1971)], an enzyme produced by *Bacillus* sp. NRRL B-3881 [Boyer, E., *J. Bacteriol.*, 110, 992 (1972)], an enzyme produced by *Streptomyces* sp. KSM-9 (Japanese Patent Application Laid-Open (kokai) No. 61-209528, an enzyme produced by *Bacillus* sp. H-167 (Japanese Patent Application Laid-Open (kokai) No. 62-208278, an enzyme produced by *Bacillus* alkalothermophilus A3-8 (Japanese Patent Application Laid-Open (kokai) No. 2-49584, and an enzyme produced by *Natronococcus* sp. Ah-36 (Japanese Patent Application Laid-Open (kokai) No. 4-211369.

As used herein, the term "alkaline α-amylase" refers to α-amylases whose optimum pHs fall within the alkaline pH range, whereas the term "alkali-resistant α-amylase" refers to α-amylases which have optimum pHs within the neutral to acidic range but whose activities in the alkaline range are comparable with those obtained at an optimum pH, and in addition, which retain their stabilities in the alkaline range. By the term "neutral range" is meant the range of pH not less than 6 and less than 8, and the term "alkaline" denotes a pH which is higher than the "neutral range".

Most of these alkaline α-amylases and alkali-resistant amylases are so-called saccharifying α-amylases which decompose starch or starch-related polysaccharides to glucose, maltose, or maltotriose. As such, these enzymes cause problems if they are used as enzymes for detergents, though they are advantageously used in the manufacture of sugar.

Thus, there remains a need for so-called alkaline liquefying α-amylases which exhibit resistance against surfactants used in detergents, and which decompose starch or starch- related polysaccharides in a highly random manner. The present inventors continued an extensive search for microorganisms producing an alkaline liquefying α-amylase suitable as a detergent component, and they discovered that an alkalophilic *Bacillus* sp. KSM-AP1378 strain, having its optimum pH for growth in the alkaline range, produces an enzyme exhibiting the activity of an alkaline liquefying α-amylase. They elucidated that this enzyme is useful as an additive in detergent compositions for washing dishes and kitchen utensils and for detergent compositions for clothes (WO94/26881).

Amounts of the enzyme produced may be effectively increased by improving a method for culturing an alkaline liquefying α-amylase-producing microorganism, *Bacillus* sp. KSM-AP1378, or by exploiting mutation. However, in order to produce the enzyme advantageously on an industrial scale, another approach must be taken.

Amounts of an enzyme produced can be enhanced using a genetic engineering approach, and in addition, the catalytic properties of the enzyme can be improved, using a protein engineering approach, by altering the gene encoding the enzyme. However, the gene encoding an alkaline liquefying α-amylase has not yet been obtained.

Accordingly, an object of the present invention is to provide the gene encoding alkaline liquefying α-amylase and fragments thereof, a transformant harboring recombinant DNA comprising the gene, and a method for producing an alkaline liquefying α-amylase using the transformant.

The DNA encoding the alkaline liquefying α-amylase gene may be further used to produce probes to be used in the isolation of additional, homologous alkaline liquefying α-amylase genes from other microorganisms. Thus, an additional object of the present invention is to provide a means of screening for and isolating additional alkaline liquefying α-amylase enzymes.

DISCLOSURE OF THE INVENTION

The present inventors attempted to isolate, from the chromosomal DNA of an alkalophilic *Bacillus* strain, a DNA fragment containing the gene encoding an alkaline liquefying α-amylase, and as a result, they were successful in isolating an approximately 1.8 kb DNA fragment encoding an alkaline liquefying α-amylase. When they transformed a host microorganism using this DNA fragment ligated to a suitable vector, it was confirmed that the resultant recombinant microorganism produced an alkaline liquefying α-amylase. Moreover, it was found that the amino acid sequence of the alkaline liquefying α-amylase to be encoded is different from that of previously known amylases. The present invention was accomplished based on this finding.

Accordingly, the present invention provides a DNA fragment encoding an alkaline liquefying α-amylase.

The present invention also provides a recombinant DNA comprising the above-described DNA fragment encoding an alkaline liquefying α-amylase.

The present invention also provides a transformed microorganism harboring the above-described recombinant DNA comprising a DNA fragment encoding an alkaline liquefying α-amylase.

The present invention further provides a method for producing an alkaline liquefying α-amylase, by culturing the above-described transformed microorganism and collecting the enzyme.

BEST MODE FOR CARRYING OUT THE INVENTION

In the present invention, a useful microorganism which serves as an alkaline liquefying α-amylase gene donor may be, for example, Bacillus sp. KSM-AP1378 (FERM BP-3048, deposited Jul. 24, 1989 in Fermentation Research Institute, Agency of Industrial Science and Technology of 1–3, Higashi 1-chome, Tsukuba-shi, Ibaraki, 305 Japan), which is an alkalophilic Bacillus strain. This strain was isolated from the soil in the vicinity of the city of Tochigi in Tochigi Prefecture, Japan by the present inventors and identified as a strain which produces significant amounts of alkaline liquefying α-amylase. This strain was deposited at the Fermentation Research Institute, Agency of Industrial Science and Technology (1–3, Higashi 1-chome, Tsukuba-shi, Ibaraki-ken, 305, Japan) under FERM BP-3048 on Aug. 8, 1990 (originally deposited as P-10886 on Jul. 24, 1989).

In order to obtain chromosomal DNA from a donor microorganism, the method proposed by Marmur, J. (*J. Mol. Biol.*, 3, 208 (1961)) or the method proposed by Saito, H. and Miura, K. (*Biochem. Biophys. Acta*, 72, 619 (1963)) may be used. Other similar methods may also be used.

DNA fragments comprising the alkaline liquefying α-amylase gene are prepared by cleaving the thus-obtained chromosomal DNA using restriction enzymes. Restriction enzymes which may be used are not particularly limited so long as they do not fragment the gene. The alkaline liquefying α-amylase gene may also be obtained by PCR (Mullis, K. B. and Faloona, F. A., *Methods Enzymol.*, 155, 335 (1987); Saiki, R. K. et al., *Science*, 239, 487 (1988). For example, the gene may be obtained through the synthesis of primers having sequences corresponding to those on the upstream side of the 5'-terminus and on the downstream side of the 3'-terminus of the essential region based on the nucleotide sequence described in Sequence No. 1, and subsequently conducting PCR using, the chromosomal DNA of an alkaline liquefying α-amylase-producing microorganism as a template. Alternatively, an intact gene may be obtained by first obtaining a fragment of the alkaline liquefying α-amylase gene from an alkaline liquefying α-amylase-producing microorganism using any procedure, followed by PCR which amplifies the upstream and downstream sides of the fragmentary gene.

The thus-prepared genetic fragment is then subjected to cloning. Host/vector systems which may be used are not particularly limited, so far as that host bacterial strains express the alkaline liquefying α-amylase gene of the present invention, that the recombinant DNA molecules can be replicated in the host bacteria, and that the integrated gene can be stably harbored. For example, members of the EK system in which the host is *E. coli* K-12, and members of the BS system in which the host is *Bacillus subtilis* Marburg, may be used. Use of the EK system, which encompasses many kinds of vectors and which is extensively studied genetically, provides good results and thus is preferred. Specific examples of host bacteria include HB101, C600, and JM109 of the EK system, and BD170, MI112, and ISW1214 of the BS system. Specific examples of vectors include pBR322 and pUC18 for the EK system, and pUB110 and pHY300PLK for the BS system.

A recombinant plasmid DNA molecule is created by cleaving a vector with a restriction enzyme followed by ligation with the above-mentioned chromosomal or PCR-amplified DNA fragment. The ligation may be achieved, for example, through the use of a DNA ligase.

Methods for transforming host bacterial strains using a recombinant DNA molecule are not particularly limited. For example, a calcium chloride method (Mandel, M. and Higa, A., *J. Mol. Biol.*, 53, 159 (1970)) may be used in the case of hosts of the EK system, and a protoplast method (Chang, C. and Cohen, S. N., *Mol. Gen. Genet.*, 168, 111 (1978)) may be used in the case of hosts of the BS system. Selection of recombinant microorganisms are performed as follows. First, microorganisms which have been transformed with DNA which contains a vector-derived DNA fragment are selected, using as an index a character which is not inactivated by insertion of exogenous chromosomal DNA fragments, such as resistance to antibiotics coded onto the vector DNA. For example, in a specific case in which pBR322 of the EK system is used as a vector, and a HindIII fragment of chromosomal DNA is inserted into the HindIII cleavage site of pBR322, the tetracycline resistant gene is inactivated, so a primary selection may be conducted by growth of the transformants that confer ampicillin resistance without having a HindIII cleavage site in the ampicillin gene. Subsequently, the selected transformants are transferred onto agar plates containing starch, using, for example, a replica method, and are then cultured so as to form colonies. By staining the starch contained in the starch-containing agar plates using an iodine-containing solution, target recombinant microorganisms can be selected as they decompose starch around the colonies.

The recombinant DNA molecule harbored by the thus-obtained recombinant microorganism can be extracted using standard procedures for preparing plasmids or phage DNAs (Maniatis, T. et al., *Molecular Cloning*, Cold Spring Harbor Laboratory, New-York (1982)). When cleavage patterns obtained through the use of various restriction enzymes are analyzed by electrophoresis, it is confirmed that the recombinant DNA molecule is a ligated product of the vector DNA molecule and a DNA fragment containing the alkaline liquefying α-amylase gene.

Figure 1:
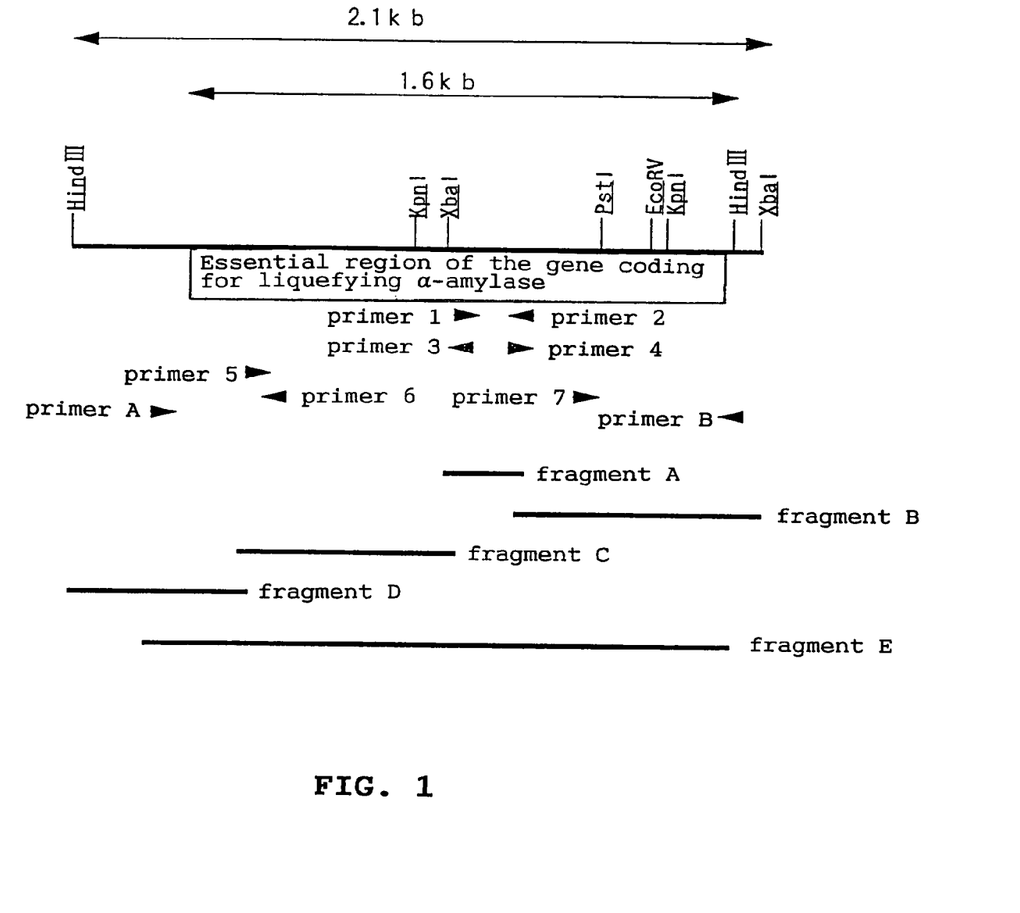
FIG. 1 shows a restriction enzyme map of a fragment of the gene encoding an alkaline liquefying amylase.

The gene encoding an alkaline liquefying α-amylase is contained in a DNA fragment of about 2.1 kb shown in the restriction enzyme map of FIG. 1, and is present in the segment of about 1.6 kb shown by the white bar. The gene has a nucleotide sequence shown as Sequence No. 1. In this sequence, the 5' terminus and 3' terminus correspond to the left-hand side and the right-hand side, respectively, of the fragment of about 2.1 kb shown as Sequence 2. In this sequence is observed an open reading frame (ORF) starting at the 145th nucleotide, ATG, and coding for a sequence consisting of 516 amino acid residues described in Sequence No. 2. Thirteen bases (13 b) upstream of the ORF, there exists a sequence AAGGAG which is highly complementary to the 3' terminal sequence of the 16S ribosomal RNA of *Bacillus subtilis* (McLaughlin, J. R. et al., *J. Biol. Chem.*, 256, 11283 (1981)). On a further upstream region extending nucleotides from 9 to 36, there exists a sequence TTGAAA . . . 16b . . . TATGGT which has high homology with the consensus sequence of a $\sigma^A$-type promoter (Gitt, M.

A. et al, *J. Biol. Chem.,* 260, 7178 (1985)). Similarly, another σ^A-type promoter sequence is found at nucleotides from 95 to 125. The amino acid sequence of the 10 amino acid residues on the amino terminus side in an alkaline liquefying α-amylase purified from a culture of *Bacillus* sp. KSM-AP1378 coincides with the sequence extending from the 37th amino acid (amino acid Nos. 37–46 in Sequence No. 1) deduced from the nucleotide sequence of the present DNA fragment.

When the nucleotide sequence of the gene of the present invention and a deduced amino acid sequence were compared with those of α-amylase known hitherto, it was confirmed that the present gene includes a novel nucleotide sequenced, with the deduced amino acid sequence encoded by the gene being different from those of other α-amylases such as a liquefying α-amylase produced by *Bacillus amylolique* (Takkinen, K. et al., *J. Biol. Chem.,* 258, 1007 (1983)), a liquefying α-amylase produced by *Bacillus stearothermophilus* (Nakajima, R. et al., *J. Bacteriol.,* 163, 401 (1985)), a liquefying α-amylase produced by *Bacillus licheniformis* (Yuuki, T et al., *J. Biochem.,* 98, 1147 (1985)), or a liquefying α-amylase produced by *Bacillus* sp. 707 (Tsukamoto, A. et al., *Biochem. Biophys. Res. Commun.,* 151, 25 (1988)).

Figure 2:
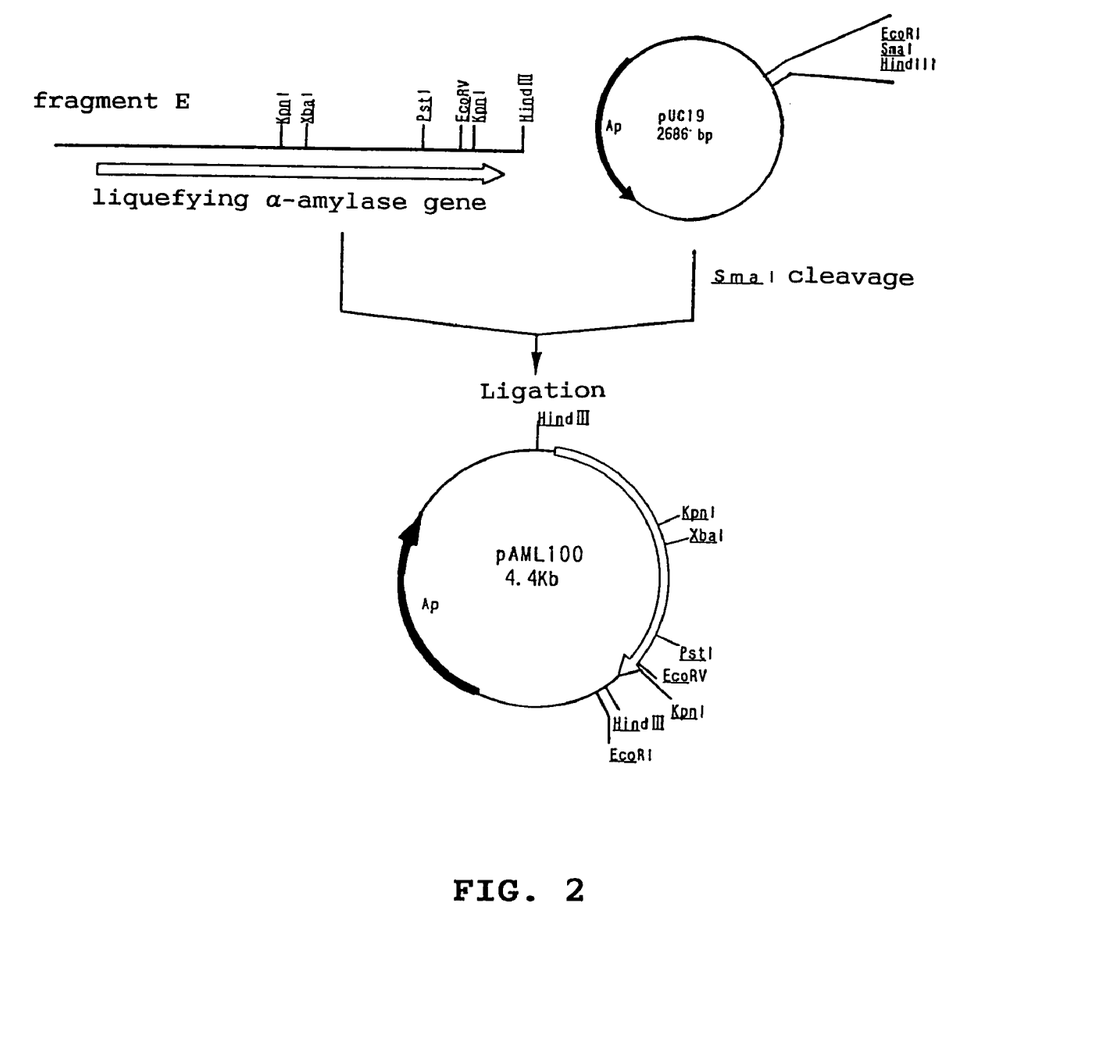
FIG. 2 is a chart depicting construction of pAML100 using a fragment of the gene encoding an alkaline liquefying amylase.
Figure 4:
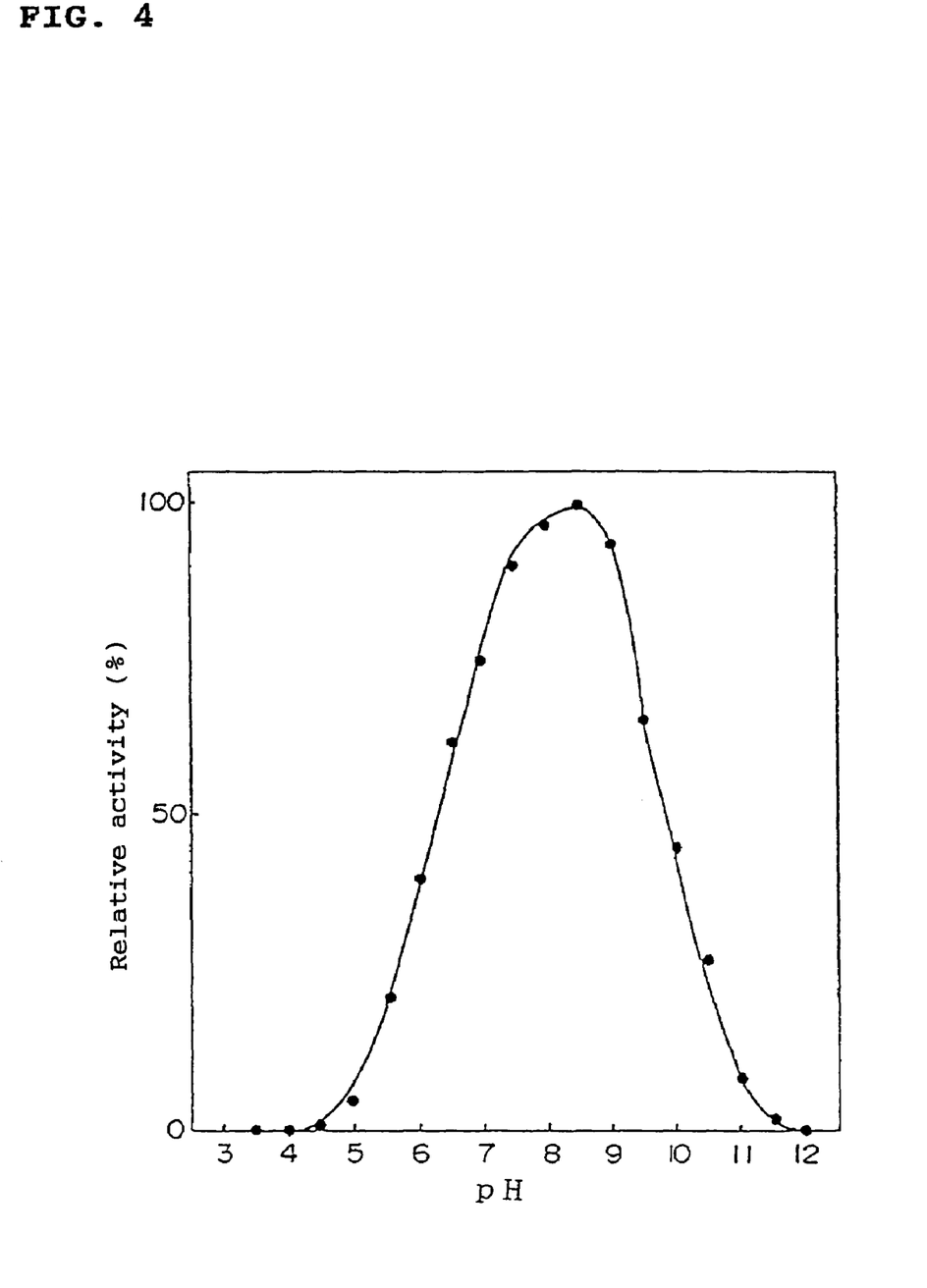
FIG. 4 is a pH profile of an alkaline liquefying α-amylase produced by Bacillus sp. KSM-AP1378.

An example of a preferred recombinant DNA molecule containing the entire region of the alkaline liquefying α-amylase gene is plasmid pAML100 (FIG. 2). This recombinant plasmid has a size of 4.4 kb and formed of a fragment containing a 1.8 kb fragment which contains the alkaline liquefying α-amylase gene and pUC19. An example of a preferred recombinant microorganism harboring the recombinant DNA molecule is an *E. coli* HB101. This strain was obtained by transforming *E. coli*, HB101 strain with the recombinant plasmid pAML100 using a standard transformation method. When this strain is cultured using a medium routinely employed for culturing *E. coli*, it produces an alkaline liquefying α-amylase. The optimum reaction pH of the thus-produced enzyme is pH 8–9. This agrees well with the activity-pH relationship profile determined for the alkaline liquefying α-amylase produced by the gene donor bacterial strain, *Bacillus* sp. KSM-AP1378 (FIG. 4).

The DNA fragments of the present invention are not necessarily limited only to those encoding the amino acid sequences shown in the below-described sequence listing, so far as they encode a protein exhibiting the enzymatic activity of interest, and they encompass DNA fragments encoding an amino acid sequence in which one or more amino acids are substituted, added, deleted, inverted, or inserted. An example of such DNA is one encoding an amino acid sequence equivalent to the amino acid sequence described in Sequence No. 2 from which up to 32 amino acids on the N-terminal side have been deleted.

In order to produce an alkaline liquefying α-amylase using the transformed microorganism of the present invention, a transformed microorganism harboring the aforementioned DNA fragment of the present invention is subjected to culturing. Alternatively, the DNA fragment may be integrated in a variety of expression vectors to obtain transformed microorganisms with enhanced expression ability, followed by culturing of the resultant transformants. Moreover, the transformed microorganisms may be cultured under different conditions depending on the identity of the microorganisms. Thus, culture conditions suited for the host may be used. In order to collect an alkaline liquefying α-amylase from the resultant culture, a routine method (such as the method described in WO94/26881) may be used.

The DNA fragments of the present invention may be further used as probes for the isolation of homologous alkaline liquefying α-amylase genes from other organisms.

EXAMPLES

The present invention will next be described in more detail by way of examples, which should not be construed as limiting the invention thereto. Concentrations in the Examples are all on a basis of % by weight.

Example 1

*Bacillus* sp. KSM-AP1378 producing an alkaline liquefying α-amylase was inoculated in 5 ml of medium A (Table 1) and subjected to shaking culture at 30° C. for 24 hours. One ml of the culture was inoculated in 100 ml of the same medium, followed by shaking culture at 30° C. for a further 12 hours. Subsequently, cells were collected by centrifugation and about 1 mg of chromosomal DNA was obtained in accordance with a method proposed by Saito and Miura (Saito, H. and Miura K., *Biochim Biophys. Acta,* 72, 619 (1963)).

TABLE 1

| Composition of medium A | |
|---|---|
| Soluble starch | 1.0% |
| Polypepton | 1.0% |
| Yeast extract | 0.5% |
| $KH_2PO_4$ | 0.1% |
| $Na_2HPO_4.12H_2O$ | 0.25% |
| $MgSO_4.7H_2O$ | 0.02% |
| $CaCl_2.2H_2O$ | 0.02% |
| $FeSO_4.7H_2O$ | 0.001% |
| $MnCl_2.4H_2O$ | 0.0001% |
| $Na_2CO_3$ | 1.0% (separately sterilized) |

Example 2

It is known that many members of the amylase family possess I–IV regions where amino acid sequences are conserved at a high level (Nakajima, R. et al., *Appl. Microbiol. Biotechnol.,* 23, 355 (1986)). Therefore, primers 1 and 2 (FIGS. 1 and 3) corresponding to regions II and IV were synthesized based on the amino acid sequence of region II and the amino acid sequence of region IV, which are particularly conserved regions among regions I through IV of known alkaline liquefying α-amylases. Using the thus-synthesized primers and chromosomal DNA of KSM-AP1378 (which served as template), PCR was conducted (one cycle=94° C.×1 min.+42° C.×1 min.+60° C.×2 min., 30 cycles). A gene fragment of approximately 0.3 kb (fragment A) shown in FIG. 1 was obtained, and the nucleotide sequence of this fragment was determined. As a result, it was found that the present fragment was coded with an amino acid sequence exhibiting a non-negligible level of homology with the amino acid sequence extending from region II through region IV of known liquefying amylase.

Example 3

Using fragment A as a probe, chromosomal DNA of XbaI-digested KSM-AP1378 was subjected to Southern hybridization. As a result, it was confirmed that there was a band which hybridized at the location of approximately 1.0 kb. An amplified fragment of approximately 0.7 kb (fragment B) was obtained by an inverse PCR method (Triglia, T. et al., *Nucleic Acids Res.,* 16, 81 (1988)) using primers synthesized from the terminal sequences of fragment A (on the side of region II: primer 3; on the side of region IV: primer 4) and DNA's which had been obtained by intramolecularly ligating XbaI-digested KSM-AP1378 chromosomal DNA (FIG. 1) as template. The nucleotide sequence of fragment B was determined, which revealed that the present fragment contained a stretch, approximately 0.6 kb region downstream from region IV. The present fragment contained a termination codon for the ORF, which was deduced to be attributed to alkaline liquefying α-amylase.

Example 4

Figure 3:
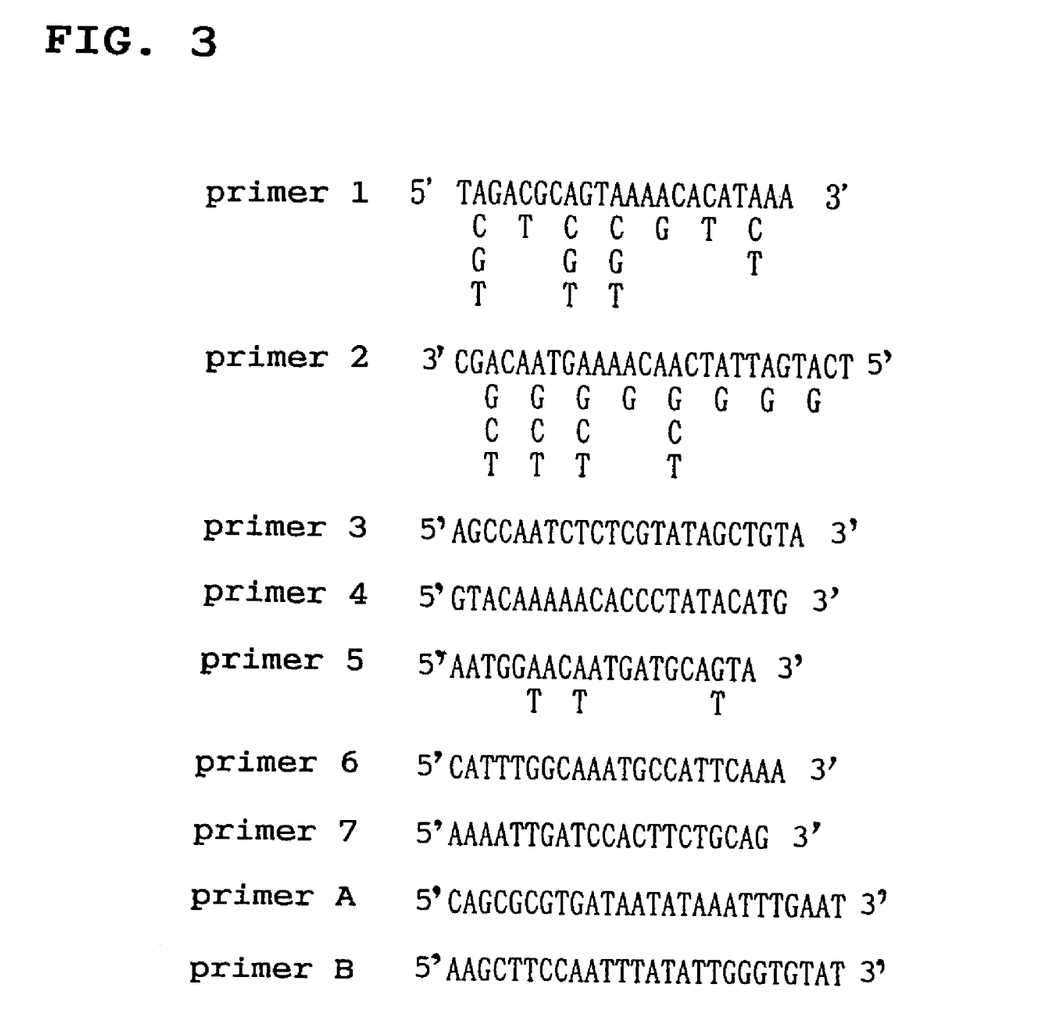
FIG. 3 shows nucleotide sequences of primers used (SEQ ID NOS: 3–11).

A primer was designed and synthesized based on the N-terminal amino acid sequence (7 amino acids) of alkaline liquefying α-amylase from the KSM-AP1378 strain (FIG. 3). Using the resultant primer (primer 5) in combination with the aforementioned primer 3 (FIG. 3) and, as a template, chromosomal DNA of KSM-AP1378, PCR was conducted to obtain a fragment of approximately 0.7 kb (fragment C, FIG. 1), thereby determining its nucleotide sequence.

Example 5

A primer containing 21 bases, stretching directly downstream of the nucleotide sequence encoding N-terminal amino acid sequence of the purified enzyme, was synthesized (primer 6). Using primers 6 and 7 (FIGS. 1 and 3) and DNAs which had been obtained by intramolecularly ligating HindIII-digested KSM-AP1378 chromosomal DNA (FIG. 1) as templates, an inverse PCR method was performed, obtaining a 1.2 kb fragment in which an upstream 0.8 kb fragment (fragment D) and a downstream PstI-HindIII 0.4 kb fragment had been ligated at the HindIII site. The nucleotide sequence of the fragment D region was determined, which revealed the presence of a signal sequence composed of 31 amino acids, MKLHNRIISVLLTLLLA-VAVLFPYMTEPAQA (from No. 1 to No. 31 of Sequence No. 2), a deduced SD sequence composed of AAGGAG (nucleotides 127–132; McLaughlin, *J. R. et al., J. Biol. Chem.,* 260, 7178 (1985)), and two kinds of deduced promoter sequences (–35 sequences, TTGAAA; –10 sequence, TATGGT, and –35 sequence, TTGACT; –10 sequence, TAAATT).

Example 6

Using primer A located at approximately 0.1 kb upstream of the promoter sequence, primer B located 79 b downstream of the termination codon, and chromosomal DNA of KSM-AP1378 as templates, a stretch of approximately 1.8 kb between the primers was amplified by PCR. The resultant amplified fragment was inserted into the SmaI site of pUC19, and then introduced into *E. coli* HB101. The transformant was allowed to grow on an LB agar medium containing 0.4% Starch azure and 15 μg/ml ampicillin. Colonies which had formed transparent halos around them were isolated as an *E. Coli* strain that produced liquefying α-amylase. A recombinant plasmid was prepared from this transformant, and a restriction enzyme map of the plasmid was made. In the map, it was confirmed that an approximately 1.8 kb DNA fragment (fragment E) shown in FIG. 1 was contained. This recombinant plasmid was designated plasmid Example 7

The recombinant *E. coli* obtained in Example 6 was subjected to shaking culture for 12 hours in 5 ml of an LB liquid medium containing 50 μg/ml of ampicillin. One (1) ml of the culture was inoculated to 100 ml of an LB medium (containing ampicillin), followed by shaking culture at 37° C. for 24 hours. Cells collected by centrifugal separation were suspended in Tris-HCl buffer (pH 8.0), and were disrupted by sonication. After the cells were sonicated, cell debris was removed by centrifugal separation, and the resultant supernatant was used as a cell-free extract. As a control, the cell-free extract of HB101 (PUC19) strain was separately prepared in a similar manner. α-Amylase activities in these extracts were measured by first causing a reaction, at 50° C. for 15 minutes, in a reaction mixture containing 50 mM glycine-NaCl-NaOH buffer (pH 10) and soluble starch, and then by quantitatively determining the produced reducing sugar by the 3,5-dinitrosalicylic acid method (WO94/26881). One unit of enzymatic activity was defined as the amount of protein that produced a quantity per minute of reducing sugar equivalent to 1 μmol of glucose. As a result, α-amylase activity was detected in the cell-free extract of strain HB101 (pAML100). The optimum working pH of α-amylase was found to fall within the pH range between 8 and 9. This result coincides well with the optimum pH of liquefying α-amylase produced by *Bacillus* sp. KSM-AP1378 (FIG. 4). For the measurement of enzymatic activities, the buffers shown in Table 2 below were used (each at 40 mM).

TABLE 2

| | |
|---|---|
| pH 3.5–5.5: | Acetate buffer |
| pH 5.5–8.5: | Tris-maleic acid buffer |
| pH 8.5–10.5: | Glycine-NaCl-NaOH buffer |
| pH 10.5–11.0: | $Na_2CO_3$—$NaHCO_3$ buffer |

INDUSTRIAL APPLICABILITY

According to the present invention, it is possible to obtain a gene encoding for alkaline liquefying α-amylase exhibiting the maximum activity in the alkaline pH range as well as a microorganism harboring such gene. Use of them facilitates mass production of alkaline liquefying α-amylase.

What is claimed is:

1. An isolated DNA molecule encoding a mutant protein exhibiting alkaline liquefying α-amylase activity at a pH optimum of 8–9 and having an amino acid sequence that differs from SEQ ID NO:2 by substitution, deletion, or insertion of one amino acid.

2. The isolated DNA molecule of claim 1, which is operably linked to a nucleotide sequence for regulating expression of the DNA molecule.

3. A recombinant DNA comprising the DNA molecule of claim 1.

4. The DNA molecule of claim 1, wherein said encoded protein has an isoelectric point higher than 8.5 when measured by isoelectric focusing electrophoresis.

5. The DNA molecule of claim 1, comprising at least one nucleotide sequence selected from the group consisting of SEQ ID NO: 10, SEQ ID NO: 7, SEQ ID NO: 3, SEQ ID NO: 6 and SEQ ID NO: 9.

6. The DNA molecule of claim 1, comprising at least one nucleotide sequence that is the reverse complement of a sequence selected from the group consisting of SEQ ID NO: 8, SEQ ID NO: 5, SEQ ID NO: 4 and SEQ ID NO: 11.

7. The DNA molecule of claim 1, comprising at least one nucleotide sequence selected from the group consisting of SEQ ID NO: 10, SEQ ID NO: 7, SEQ ID NO: 3, SEQ ID NO: 6 and SEQ ID NO: 9, and also comprising at least one nucleotide sequence that is the reverse complement of a sequence selected from the group consisting of SEQ ID NO: 8, SEQ ID NO: 5, SEQ ID NO: 4 and SEQ ID NO: 11.

* * * * *

SEQUENCE LISTING

<160> NUMBER OF SEQ ID NOS: 11

<210> SEQ ID NO 1
<211> LENGTH: 1776

```
<212> TYPE: DNA
<213> ORGANISM: Bacillus sp.
<220> FEATURE:
<221> NAME/KEY: CDS
<222> LOCATION: (145)..(1692)

<400> SEQUENCE: 1
atataaattt gaaatgaaca cctatgaaaa tatggtagcg attgcgcgac gagaaaaaac         60
ttgggagtta ggaagtgata ttaaaggatt tttttttgact tgttgtgaaa acgcttgcat       120
aaattgaagg agagggtgct tttt atg aaa ctt cat aac cgt ata att agc          171
                          Met Lys Leu His Asn Arg Ile Ile Ser
                            1               5 gta cta tta aca cta ttg tta gct gta gct gtt ttg ttt cca tat atg         219
Val Leu Leu Thr Leu Leu Leu Ala Val Ala Val Leu Phe Pro Tyr Met
 10              15                  20                  25 acg gaa cca gca caa gcc cat cat aat ggg acg aat ggg acc atg atg         267
Thr Glu Pro Ala Gln Ala His His Asn Gly Thr Asn Gly Thr Met Met
                 30                  35                  40 cag tat ttt gaa tgg cat ttg cca aat gac ggg aac cac tgg aac agg         315
Gln Tyr Phe Glu Trp His Leu Pro Asn Asp Gly Asn His Trp Asn Arg
             45                  50                  55 tta cga gat gac gca gct aac tta aag agt aaa ggg att acc gct gtt         363
Leu Arg Asp Asp Ala Ala Asn Leu Lys Ser Lys Gly Ile Thr Ala Val
         60                  65                  70 tgg att cct cct gca tgg aag ggg act tcg caa aat gat gtt ggg tat         411
Trp Ile Pro Pro Ala Trp Lys Gly Thr Ser Gln Asn Asp Val Gly Tyr
     75                  80                  85 ggt gcc tat gat ttg tac gat ctt ggt gag ttt aac caa aag gga acc         459
Gly Ala Tyr Asp Leu Tyr Asp Leu Gly Glu Phe Asn Gln Lys Gly Thr
 90                  95                 100                 105 gtc cgt aca aaa tat ggc aca agg agt cag ttg caa ggt gcc gtg aca         507
Val Arg Thr Lys Tyr Gly Thr Arg Ser Gln Leu Gln Gly Ala Val Thr
                110                 115                 120 tct ttg aaa aat aac ggg att caa gtt tat ggg gat gtc gtg atg aat         555
Ser Leu Lys Asn Asn Gly Ile Gln Val Tyr Gly Asp Val Val Met Asn
            125                 130                 135 cat aaa ggt gga gca gac ggg aca gag atg gta aat gcg gtg gaa gtg         603
His Lys Gly Gly Ala Asp Gly Thr Glu Met Val Asn Ala Val Glu Val
        140                 145                 150 aac cga agc aac cga aac caa gaa ata tca ggt gaa tac acc att gaa         651
Asn Arg Ser Asn Arg Asn Gln Glu Ile Ser Gly Glu Tyr Thr Ile Glu
    155                 160                 165 gca tgg acg aaa ttt gat ttc cct gga aga gga aat acc cat tcc aac         699
Ala Trp Thr Lys Phe Asp Phe Pro Gly Arg Gly Asn Thr His Ser Asn
170                 175                 180                 185 ttt aaa tgg cgc tgg tat cat ttt gat ggg aca gat tgg gat cag tca         747
Phe Lys Trp Arg Trp Tyr His Phe Asp Gly Thr Asp Trp Asp Gln Ser
                190                 195                 200 cgt cag ctt cag aac aaa ata tat aaa ttc aga ggt acc gga aag gca         795
Arg Gln Leu Gln Asn Lys Ile Tyr Lys Phe Arg Gly Thr Gly Lys Ala
            205                 210                 215 tgg gac tgg gaa gta gat ata gag aac ggc aac tat gat tac ctt atg         843
Trp Asp Trp Glu Val Asp Ile Glu Asn Gly Asn Tyr Asp Tyr Leu Met
        220                 225                 230 tat gca gac att gat atg gat cat cca gaa gta atc aat gaa ctt aga         891
Tyr Ala Asp Ile Asp Met Asp His Pro Glu Val Ile Asn Glu Leu Arg
    235                 240                 245 aat tgg gga gtt tgg tat aca aat aca ctt aat cta gat gga ttt aga         939
Asn Trp Gly Val Trp Tyr Thr Asn Thr Leu Asn Leu Asp Gly Phe Arg
250                 255                 260                 265
```

| | |
|---|---|
| atc gat gct gtg aaa cat att aaa tac agc tat acg aga gat tgg cta<br>Ile Asp Ala Val Lys His Ile Lys Tyr Ser Tyr Thr Arg Asp Trp Leu<br>         270        275        280 | 987 |
| aca cat gtg cgt aac acc aca ggt aaa cca atg ttt gca gtt gca gaa<br>Thr His Val Arg Asn Thr Thr Gly Lys Pro Met Phe Ala Val Ala Glu<br>285           290        295 | 1035 |
| ttt tgg aaa aat gac ctt gct gca atc gaa aac tat tta aat aaa aca<br>Phe Trp Lys Asn Asp Leu Ala Ala Ile Glu Asn Tyr Leu Asn Lys Thr<br>    300         305        310 | 1083 |
| agt tgg aat cac tcc gtg ttc gat gtt cct ctt cat tat aat ttg tac<br>Ser Trp Asn His Ser Val Phe Asp Val Pro Leu His Tyr Asn Leu Tyr<br>315           320        325 | 1131 |
| aat gca tct aat agt ggt ggc tat ttt gat atg aga aat att tta aat<br>Asn Ala Ser Asn Ser Gly Gly Tyr Phe Asp Met Arg Asn Ile Leu Asn<br>330           335        340        345 | 1179 |
| ggt tct gtc gta caa aaa cac cct ata cat gca gtc aca ttt gtt gat<br>Gly Ser Val Val Gln Lys His Pro Ile His Ala Val Thr Phe Val Asp<br>         350        355        360 | 1227 |
| aac cat gac tct cag cca gga gaa gca ttg gaa tcc ttt gtt caa tcg<br>Asn His Asp Ser Gln Pro Gly Glu Ala Leu Glu Ser Phe Val Gln Ser<br>    365         370        375 | 1275 |
| tgg ttc aaa cca ctg gca tat gca ttg att ctg aca agg gag caa ggt<br>Trp Phe Lys Pro Leu Ala Tyr Ala Leu Ile Leu Thr Arg Glu Gln Gly<br>380           385        390 | 1323 |
| tac cct tcc gta ttt tac ggt gat tac tac ggt ata cca act cat ggt<br>Tyr Pro Ser Val Phe Tyr Gly Asp Tyr Tyr Gly Ile Pro Thr His Gly<br>395           400        405 | 1371 |
| gtt cct tcg atg aaa tct aaa att gat cca ctt ctg cag gca cgt caa<br>Val Pro Ser Met Lys Ser Lys Ile Asp Pro Leu Leu Gln Ala Arg Gln<br>410           415        420        425 | 1419 |
| acg tat gcc tac gga acc caa cat gat tat ttt gat cat cat gat att<br>Thr Tyr Ala Tyr Gly Thr Gln His Asp Tyr Phe Asp His His Asp Ile<br>         430        435        440 | 1467 |
| atc ggc tgg acg aga gaa ggg gac agc tcc cac cca aat tca gga ctt<br>Ile Gly Trp Thr Arg Glu Gly Asp Ser Ser His Pro Asn Ser Gly Leu<br>    445         450        455 | 1515 |
| gca act att atg tcc gat ggg cca ggg ggt aat aaa tgg atg tat gtc<br>Ala Thr Ile Met Ser Asp Gly Pro Gly Gly Asn Lys Trp Met Tyr Val<br>460           465        470 | 1563 |
| ggg aaa cat aaa gct ggc caa gta tgg aga gat atc acc gga aat agg<br>Gly Lys His Lys Ala Gly Gln Val Trp Arg Asp Ile Thr Gly Asn Arg<br>475           480        485 | 1611 |
| tct ggt acc gtc acc att aat gca gat ggt tgg ggg aat ttc act gta<br>Ser Gly Thr Val Thr Ile Asn Ala Asp Gly Trp Gly Asn Phe Thr Val<br>490           495        500        505 | 1659 |
| aac gga ggg gca gtt tcg gtt tgg gtg aag caa taaataagga acaagaggcg<br>Asn Gly Gly Ala Val Ser Val Trp Val Lys Gln<br>         510        515 | 1712 |
| aaaattactt tcctacatgc agagctttcc gatcactcat acacccaata taaattggaa | 1772 |
| gctt | 1776 |

<210> SEQ ID NO 2
<211> LENGTH: 516
<212> TYPE: PRT
<213> ORGANISM: Bacillus sp.

<400> SEQUENCE: 2

Met Lys Leu His Asn Arg Ile Ile Ser Val Leu Leu Thr Leu Leu Leu
1       5         10         15

-continued

Ala Val Ala Val Leu Phe Pro Tyr Met Thr Glu Pro Ala Gln Ala His
            20                  25                  30

His Asn Gly Thr Asn Gly Thr Met Met Gln Tyr Phe Glu Trp His Leu
        35                  40                  45

Pro Asn Asp Gly Asn His Trp Asn Arg Leu Arg Asp Asp Ala Ala Asn
    50                  55                  60

Leu Lys Ser Lys Gly Ile Thr Ala Val Trp Ile Pro Pro Ala Trp Lys
65                  70                  75                  80

Gly Thr Ser Gln Asn Asp Val Gly Tyr Gly Ala Tyr Asp Leu Tyr Asp
                85                  90                  95

Leu Gly Glu Phe Asn Gln Lys Gly Thr Val Arg Thr Lys Tyr Gly Thr
            100                 105                 110

Arg Ser Gln Leu Gln Gly Ala Val Thr Ser Leu Lys Asn Asn Gly Ile
            115                 120                 125

Gln Val Tyr Gly Asp Val Val Met Asn His Lys Gly Gly Ala Asp Gly
        130                 135                 140

Thr Glu Met Val Asn Ala Val Glu Val Asn Arg Ser Asn Arg Asn Gln
145                 150                 155                 160

Glu Ile Ser Gly Glu Tyr Thr Ile Glu Ala Trp Thr Lys Phe Asp Phe
                165                 170                 175

Pro Gly Arg Gly Asn Thr His Ser Asn Phe Lys Trp Arg Trp Tyr His
            180                 185                 190

Phe Asp Gly Thr Asp Trp Asp Gln Ser Arg Gln Leu Gln Asn Lys Ile
        195                 200                 205

Tyr Lys Phe Arg Gly Thr Gly Lys Ala Trp Asp Trp Glu Val Asp Ile
    210                 215                 220

Glu Asn Gly Asn Tyr Asp Tyr Leu Met Tyr Ala Asp Ile Asp Met Asp
225                 230                 235                 240

His Pro Glu Val Ile Asn Glu Leu Arg Asn Trp Gly Val Trp Tyr Thr
                245                 250                 255

Asn Thr Leu Asn Leu Asp Gly Phe Arg Ile Asp Ala Val Lys His Ile
            260                 265                 270

Lys Tyr Ser Tyr Thr Arg Asp Trp Leu Thr His Val Arg Asn Thr Thr
        275                 280                 285

Gly Lys Pro Met Phe Ala Val Ala Glu Phe Trp Lys Asn Asp Leu Ala
    290                 295                 300

Ala Ile Glu Asn Tyr Leu Asn Lys Thr Ser Trp Asn His Ser Val Phe
305                 310                 315                 320

Asp Val Pro Leu His Tyr Asn Leu Tyr Asn Ala Ser Asn Ser Gly Gly
                325                 330                 335

Tyr Phe Asp Met Arg Asn Ile Leu Asn Gly Ser Val Val Gln Lys His
            340                 345                 350

Pro Ile His Ala Val Thr Phe Val Asp Asn His Asp Ser Gln Pro Gly
        355                 360                 365

Glu Ala Leu Glu Ser Phe Val Gln Ser Trp Phe Lys Pro Leu Ala Tyr
    370                 375                 380

Ala Leu Ile Leu Thr Arg Glu Gln Gly Tyr Pro Ser Val Phe Tyr Gly
385                 390                 395                 400

Asp Tyr Tyr Gly Ile Pro Thr His Gly Val Pro Ser Met Lys Ser Lys
                405                 410                 415

Ile Asp Pro Leu Leu Gln Ala Arg Gln Thr Tyr Ala Tyr Gly Thr Gln
            420                 425                 430

```
His Asp Tyr Phe Asp His His Asp Ile Ile Gly Trp Thr Arg Glu Gly
        435                 440                 445

Asp Ser Ser His Pro Asn Ser Gly Leu Ala Thr Ile Met Ser Asp Gly
    450                 455                 460

Pro Gly Gly Asn Lys Trp Met Tyr Val Gly Lys His Lys Ala Gly Gln
465                 470                 475                 480

Val Trp Arg Asp Ile Thr Gly Asn Arg Ser Gly Thr Val Thr Ile Asn
                485                 490                 495

Ala Asp Gly Trp Gly Asn Phe Thr Val Asn Gly Gly Ala Val Ser Val
            500                 505                 510

Trp Val Lys Gln
        515

<210> SEQ ID NO 3
<211> LENGTH: 22
<212> TYPE: DNA
<213> ORGANISM: Artificial Sequence
<220> FEATURE:
<223> OTHER INFORMATION: any n = a,c,t or g
<220> FEATURE:
<223> OTHER INFORMATION: Description of Artificial Sequence:Primer

<400> SEQUENCE: 3
tngaygcngt naarcayath aa                                          22

<210> SEQ ID NO 4
<211> LENGTH: 26
<212> TYPE: DNA
<213> ORGANISM: Artificial Sequence
<220> FEATURE:
<223> OTHER INFORMATION: any n = a,c,t or g
<220> FEATURE:
<223> OTHER INFORMATION: Description of Artificial Sequence:Primer

<400> SEQUENCE: 4
tcrtgrttrt cnacraangt nacngc                                      26

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence:Primer

<400> SEQUENCE: 5
agccaatctc tcgtatagct gta                                         23

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence:Primer

<400> SEQUENCE: 6
gtacaaaaac accctataca tg                                          22

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 7
```

```
aatggwacwa tgatgcakta                                              20

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence:Primer

<400> SEQUENCE: 8
catttggcaa atgccattca aa                                           22

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:Primer

<400> SEQUENCE: 9
aaaattgatc cacttctgca g                                            21

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence:Primer

<400> SEQUENCE: 10
cagcgcgtga taatataaat ttgaat                                       26

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence:Primer

<400> SEQUENCE: 11
aagcttccaa tttatattgg gtgtat                                       26
```